(12) United States Patent
Sung et al.

(10) Patent No.: US 10,418,300 B2
(45) Date of Patent: *Sep. 17, 2019

(54) SUBSTRATE STRUCTURE AND METHOD FOR PREPARING THE SAME

(71) Applicant: IUCF-HYU (INDUSTRY-UNIVERSITY COOPERATION FOUNDATION HANYANG UNIVERSITY), Seoul (KR)

(72) Inventors: Myung Mo Sung, Seoul (KR); Kyu Seok Han, Seoul (KR)

(73) Assignee: IUCF-HYU (INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 443 days.

This patent is subject to a terminal disclaimer.

(21) Appl. No.: 14/915,562

(22) PCT Filed: Nov. 4, 2013

(86) PCT No.: PCT/KR2013/009910
§ 371 (c)(1),
(2) Date: Feb. 29, 2016

(87) PCT Pub. No.: WO2015/030298
PCT Pub. Date: Mar. 5, 2015

(65) Prior Publication Data
US 2016/0215394 A1 Jul. 28, 2016

(30) Foreign Application Priority Data
Aug. 30, 2013 (KR) .................. 10-2013-0104463

(51) Int. Cl.
C23C 16/455 (2006.01)
G02F 1/1333 (2006.01)
(Continued)

(52) U.S. Cl.
CPC ............ H01L 23/3192 (2013.01); C07F 3/06 (2013.01); C07F 5/062 (2013.01);
(Continued)

(58) Field of Classification Search
CPC . H01L 23/3192; H01L 23/293; H01L 21/563; H01L 51/5253; H01L 51/005;
(Continued)

(56) References Cited

U.S. PATENT DOCUMENTS 7,951,458 B2    5/2011  Ogura et al.
8,124,179 B2    2/2012  Nilsen et al.
(Continued)

FOREIGN PATENT DOCUMENTS

CN    102027603 A    4/2011
JP    2002-53669 A    2/2002
(Continued)

OTHER PUBLICATIONS

Kanaizuka, K., Haruki, R., Sakata, O., Yoshimoto, M., Akita, Y., & Kitagawa, H. (2008). Construction of highly oriented crystalline surface coordination polymers composed of copper dithiooxamide complexes. Journal of the American Chemical Society, 130(47), 15778-15779. (Year: 2008).*
(Continued)

*Primary Examiner* — Frank J Vineis
*Assistant Examiner* — Michael Zhang
(74) *Attorney, Agent, or Firm* — Oblon, McClelland, Maier & Neustadt, L.L.P.

(57) ABSTRACT

The present invention relates to a substrate structure in which organic-inorganic hybrid thin films are laminated and
(Continued)

a method for preparing the same and more specifically to a substrate structure in which organic-inorganic hybrid thin films are laminated that can be used for light emitters, display devices and solar cell devices wherein the organic-inorganic hybrid thin film including a stable new functional group, an inorganic precursor and an organic precursor are alternately used to afford stability in air and a method for preparing the same.

20 Claims, 8 Drawing Sheets

(51) Int. Cl.
| | |
|---|---|
| H01L 51/00 | (2006.01) |
| H01L 51/52 | (2006.01) |
| H01L 23/31 | (2006.01) |
| C07F 5/06 | (2006.01) |
| H01L 31/0203 | (2014.01) |
| C07F 3/06 | (2006.01) |
| H01L 21/56 | (2006.01) |
| H01L 23/29 | (2006.01) |

(52) U.S. Cl.
CPC .. *C23C 16/45529* (2013.01); *C23C 16/45553* (2013.01); *G02F 1/1333* (2013.01); *G02F 1/133305* (2013.01); *H01L 21/563* (2013.01); *H01L 23/293* (2013.01); *H01L 31/0203* (2013.01); *H01L 51/005* (2013.01); *H01L 51/0034* (2013.01); *H01L 51/0096* (2013.01); *H01L 51/5253* (2013.01); *G02F 1/133345* (2013.01); *G02F 2001/133302* (2013.01); *G02F 2201/501* (2013.01); *G02F 2202/022* (2013.01); *H01L 2251/301* (2013.01); *H01L 2251/305* (2013.01); *H01L 2251/308* (2013.01); *H01L 2251/558* (2013.01)

(58) Field of Classification Search
CPC ............. H01L 51/0034; H01L 51/0096; H01L 31/0203; H01L 2251/308; H01L 2251/305; H01L 2251/558; H01L 2251/301; C07F 5/062; C07F 3/06; C23C 16/45529; C23C 16/45553; G02F 1/133305; G02F 1/1333; G02F 1/133345; G02F 2201/501; G02F 2201/133302; G02F 2202/022

See application file for complete search history.

(56) References Cited

U.S. PATENT DOCUMENTS

| | | |
|---|---|---|
| 2005/0153077 A1 | 7/2005 | Gedeon et al. |
| 2009/0081883 A1 | 3/2009 | Freeman et al. |
| 2009/0217975 A1* | 9/2009 | Kalberlah ............. H01L 31/048 136/256 |
| 2010/0178481 A1* | 7/2010 | George ................. C23C 16/402 428/213 |

FOREIGN PATENT DOCUMENTS

| | | | |
|---|---|---|---|
| JP | 2005-289885 | A | 10/2005 |
| JP | 2008-255242 | A | 10/2008 |
| JP | 2011-506758 | A | 3/2011 |
| JP | 2012-171291 | A | 9/2012 |
| JP | 5220106 | B2 | 6/2013 |
| KR | 10-2007-0095919 | A | 10/2007 |
| KR | 10-2012-0128113 | A | 11/2012 |
| WO | WO 2011/115147 | A1 | 9/2011 |

OTHER PUBLICATIONS

T. Kawahara, et al., "Synthesis of a Net-Worked Strontium-O-Phenylene-S-Tellurium Hybrid Co-polymer Having a Two-Step Electron Transfer Nature", Designed Monomers and Polymers, vol. 11, No. 1, 2008, pp. 47-55 and cover page.

Hideo Matsui, et al., "Syntheses and Electronic Behaviors of Several Phenylene-Chromium, -Molybdenum and/or -Tungsten Hybrid Copolymers", Journal of Macromolecular Science, Part A: Pure and Applied Chemistry, vol. 42, No. 6, 2005, pp. 733-740.

T. L. Freeman, et al., "Multilayers of ω-mercaptoalkanoic acids containing a polar aromatic group: characterization of films" Thin Solid Films, vol. 244, May 1994, XP025732398, pp. 784-788.

Mathias Brust, et al., "Self-Assembly of Photoluminescent Copper(I)-Dithiol Multilayer Thin Films and Bulk Materials" Langmuir, vol. 13, No. 21, Oct. 1997, XP055351602, pp. 5602-5607 and cover page.

Minwoo Park, et al., "Gas diffusion barrier characteristics of $Al_2O_3$/alucone films formed using trimethylaluminum, water and ethylene glycol for organic light emitting diode encapsulation" Thin Solid Films, vol. 546, May 2013, pp. 153-156.

International Search Report dated May 19, 2014 in PCT/KR2013/009910 filed Nov. 4, 2013.

\* cited by examiner

[Fig. 1]
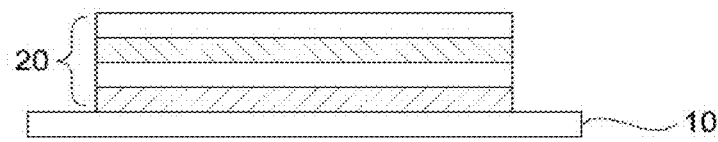
[Fig. 2]
[Fig. 3]
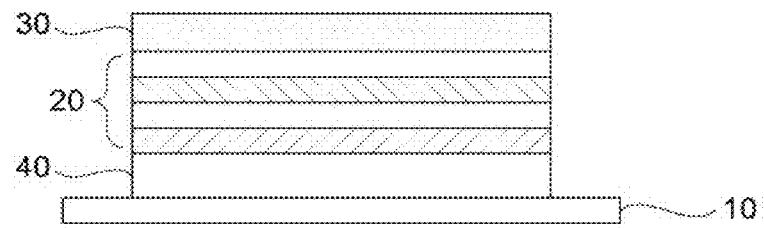
[Fig. 4]
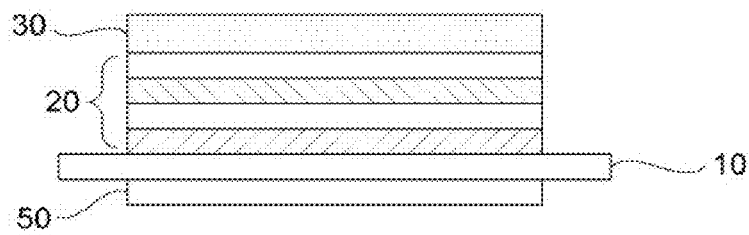
[Fig. 5]
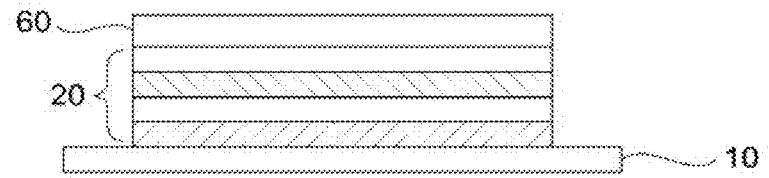
[Fig. 6]
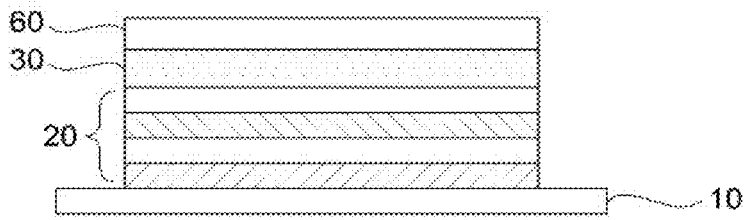

[Fig. 7]
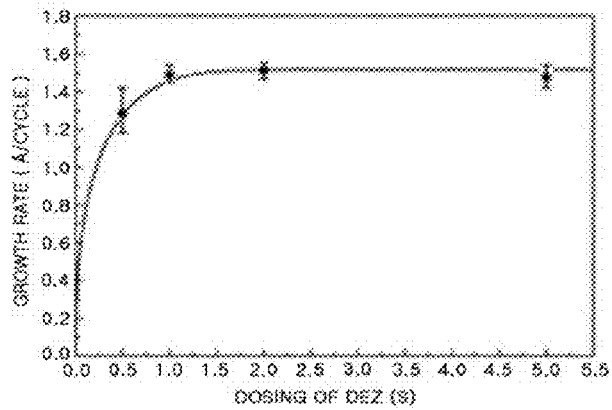
[Fig. 8]
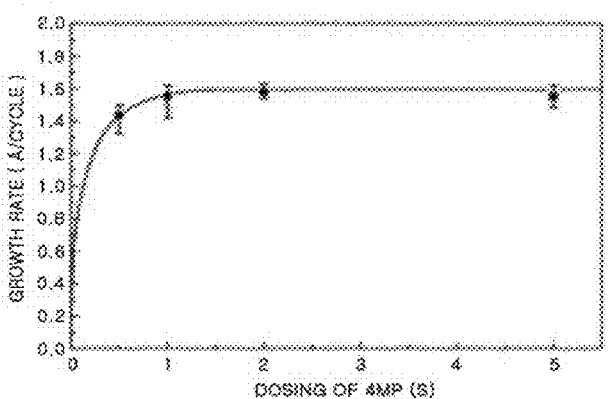
[Fig. 9]
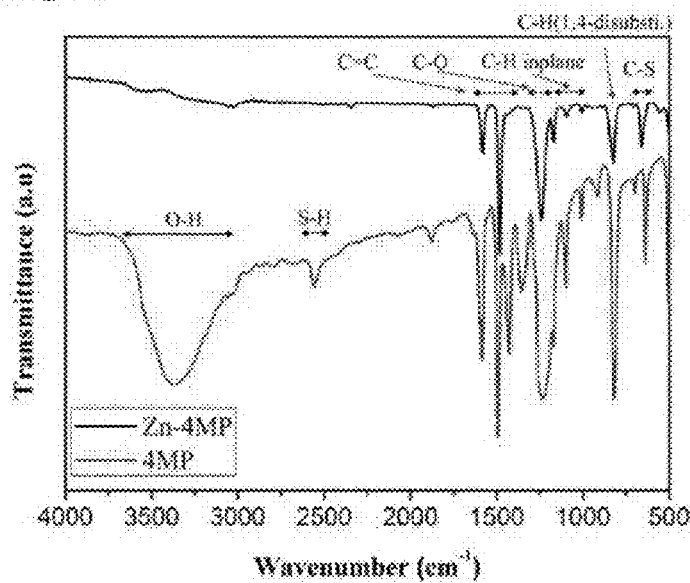

[Fig. 10]
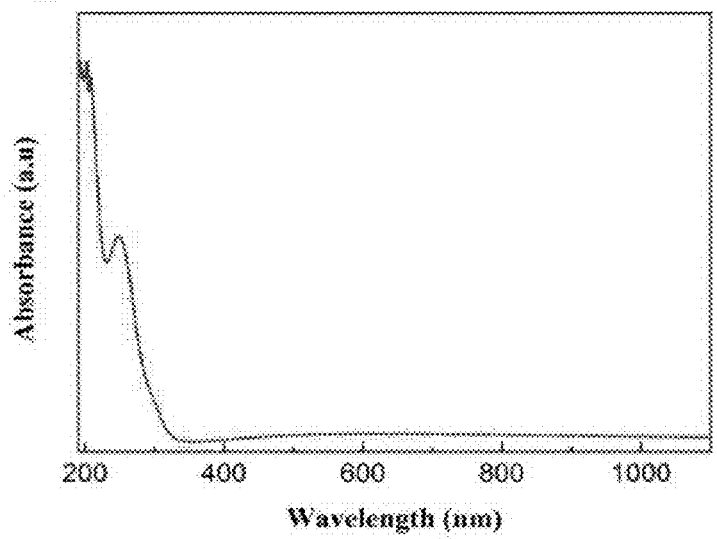
[Fig. 11]
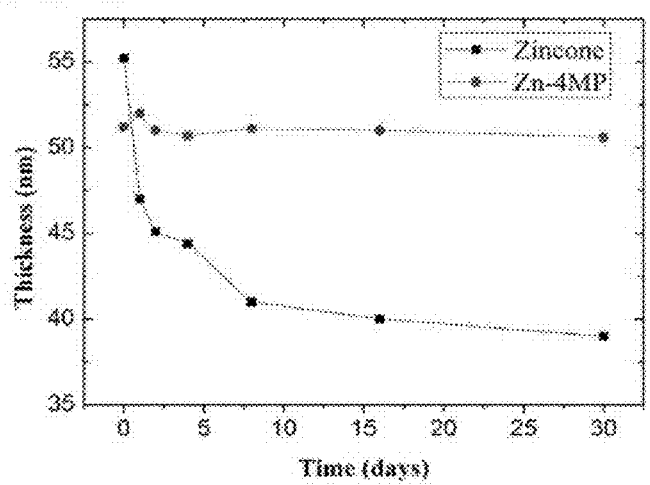
[Fig. 12]
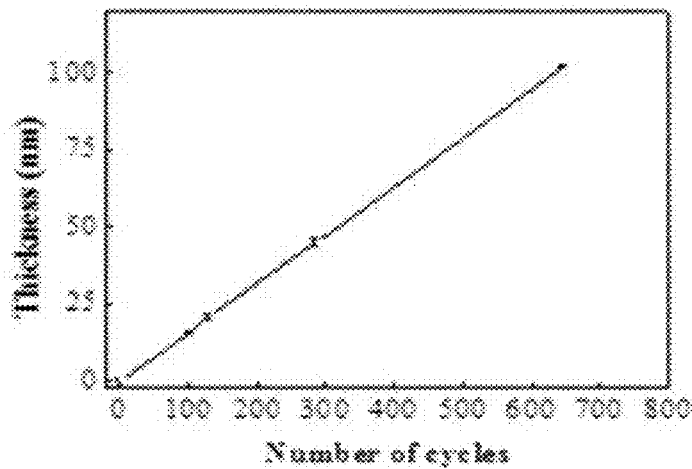

[Fig. 13]
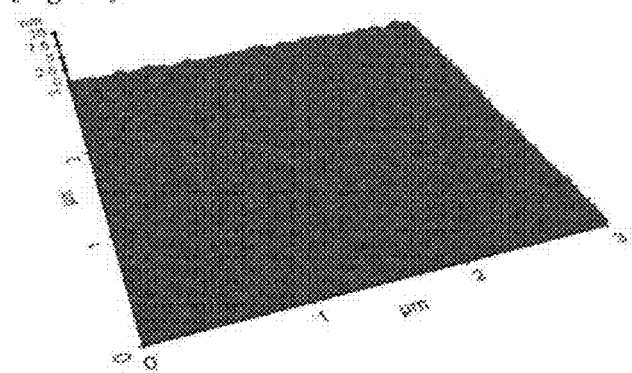
[Fig. 14]
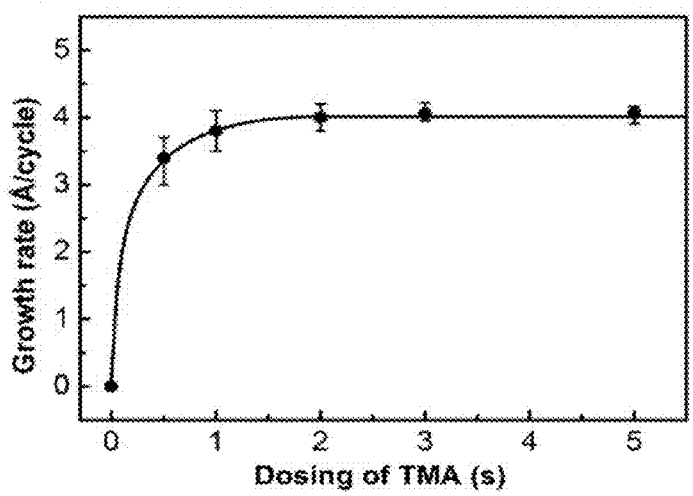
[Fig. 15]
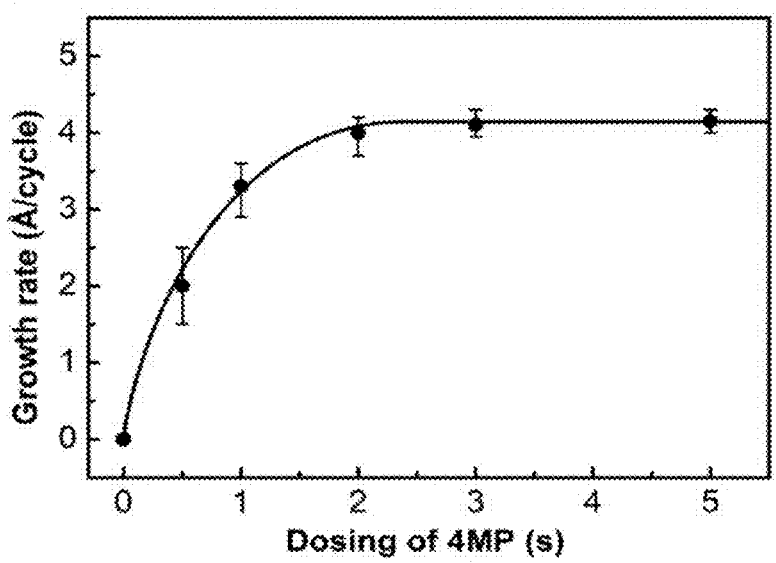

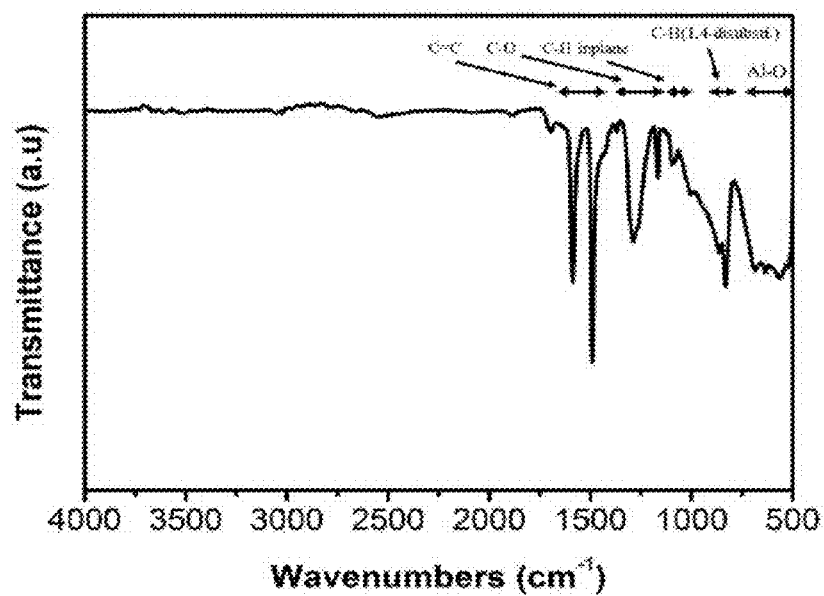
[Fig. 16]
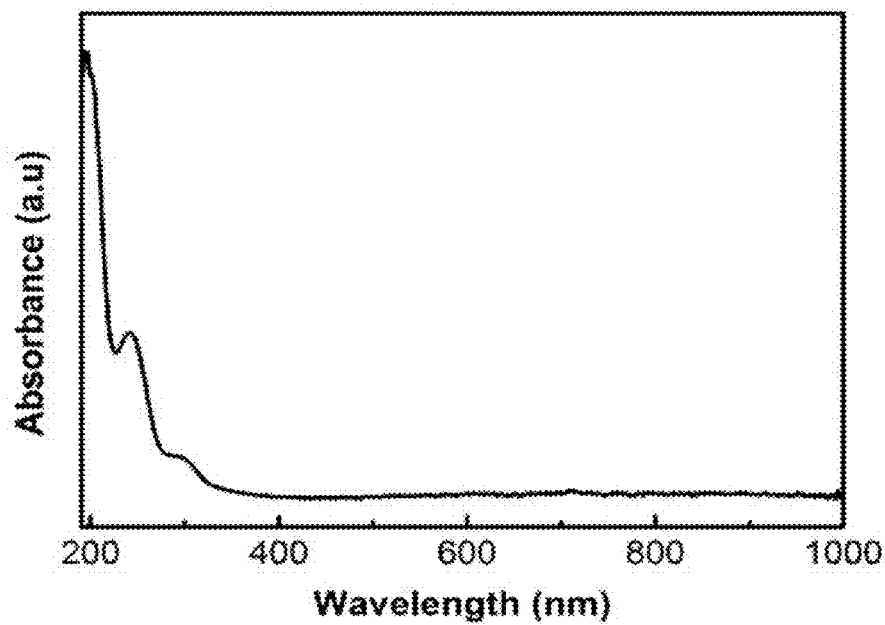
[Fig. 17]

[Fig. 18]
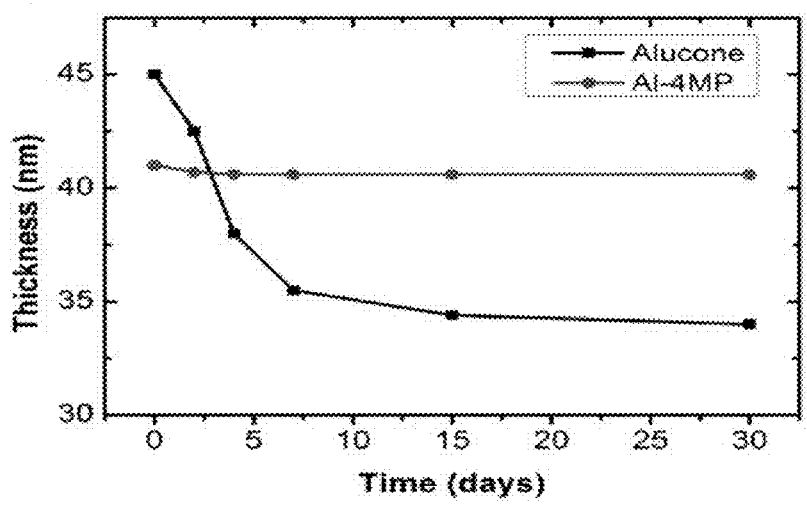
[Fig. 19]
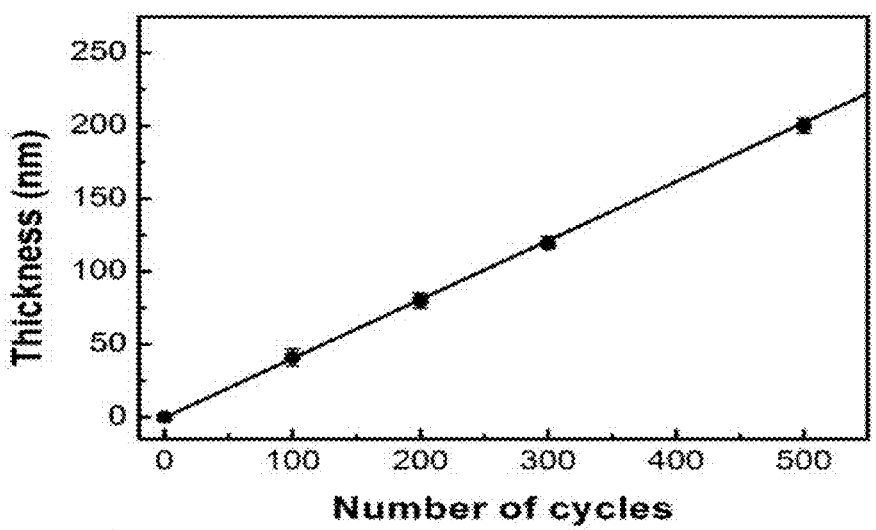
[Fig. 20]
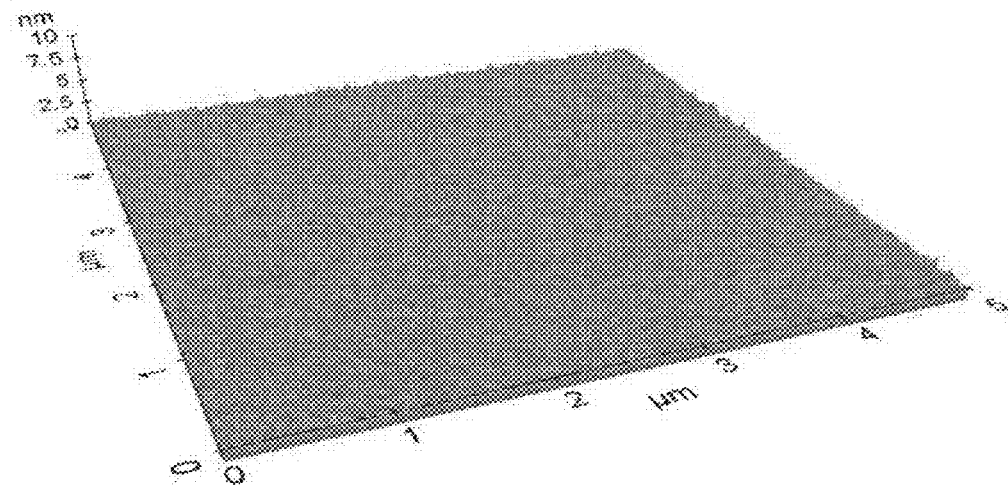

[Fig. 21]
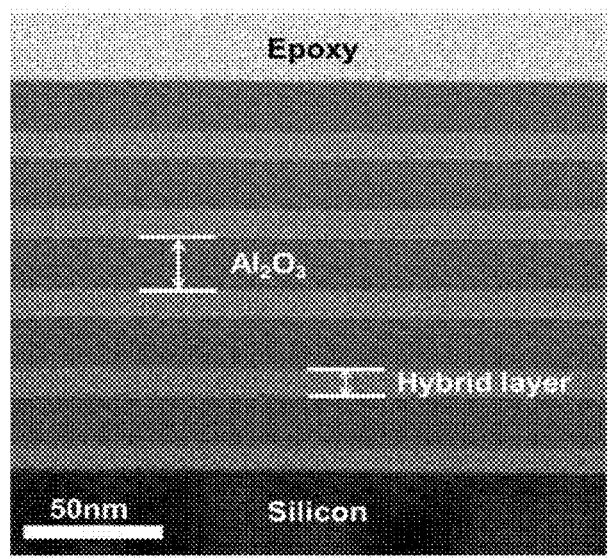
[Fig. 22]
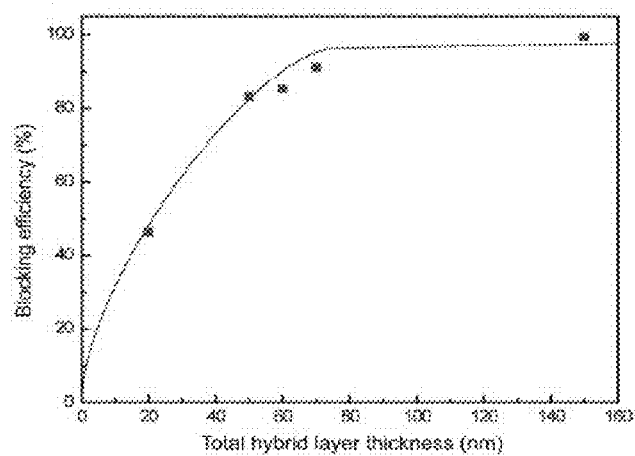
[Fig. 23]
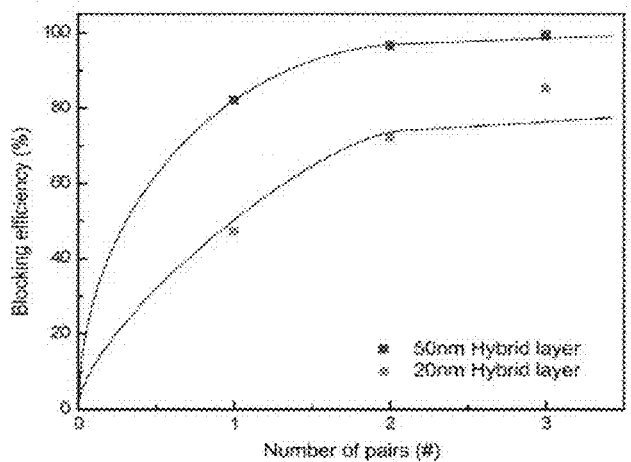

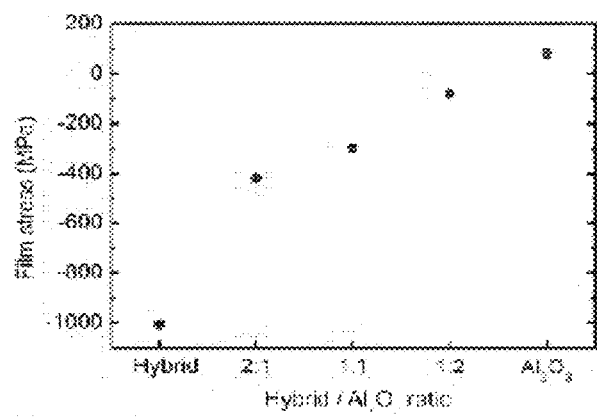

SUBSTRATE STRUCTURE AND METHOD FOR PREPARING THE SAME

TECHNICAL FIELD

The present invention relates to a substrate structure and a method for preparing the same and more specifically to a substrate structure including a stable new functional group in which an organic-inorganic hybrid thin film formed by the molecular layer deposition method alternately using inorganic precursor and organic precursor is laminated and a method for preparing the same.

BACKGROUND TECHNOLOGY

While the glass substrate used for display purposes, frames, crafts, containers, etc. has a number of advantages including a small linear expansion coefficient, excellent gas barrier properties, high optical transmittance, surface flatness, and superior heat resistance and chemical resistance, it has shortcomings such as being fragile, and therefore easily broken by impact, and heavy due to its high density.

As interest in liquid crystal, organic luminescence displays or electronic paper has recently increased drastically, studies in which substrates of such display devices are replaced with plastics are actively carried out. That is, if a glass substrate is replaced with a plastic substrate, the total weight of a display becomes lighter and flexibility of design may be afforded. In addition, it is resistant to impact and if it is manufactured in a continuous process, it may have economic advantages over the glass substrate.

On the other hand, in order for the plastic substrate to be used for a display, certain characteristics are required, such as high glass transition temperature, blocking of oxygen water vapour for preventing aging of liquid crystal and organic luminescent material, low linear expansion coefficient and dimensional stability for preventing distortion of a substrate caused by changes in a process temperature, high mechanical strength for being compatible with process instruments used for the existing glass substrate, chemical resistance for withstanding an etching process, high optical transmission and small birefringence, and surface scratch resistance.

However, since no polymeric film or highly functional polymeric substrate film including a polymeric-inorganic hybrid film exists, such studies are being conducted in which a number of functional coatings are made on a polymeric substrate film to satisfy the above physical properties.

Organic-inorganic hybrid materials are such materials that are able to exhibit both properties of an organic material and properties of an inorganic material by binding the organic material with the inorganic material based on a physical or chemical method.

The method that has been used the most to prepare the organic-inorganic hybrid thin film is the sol-gel method and it enables the easy preparation of organic-inorganic hybrid materials at low temperatures with the result that research thereon has been carried out extensively for a long time. Nevertheless, the sol-gel method has shortcomings such that it is difficult to control in terms of a monomolecular layer and that deformation occurs following thermal treatment, which makes it difficult to prepare an organic-inorganic hybrid thin film of high quality.

Another method for preparing the organic-inorganic hybrid thin film is based on intercalation and enables the preparation of the organic-inorganic hybrid material which was difficult to prepare by the sol-gel method. Nevertheless, because this method is also difficult to control in terms of a monomolecular layer and has slow deposition rates, it presents difficulties when preparing an organic-inorganic nano hybrid super-lattice of high quality.

The molecular self-assembly method prepares an organic-inorganic hybrid thin film by using static electricity and is a very useful method that enables polymer, nanoparticles, nanoplate, etc. to be grown in a layer form. Much effort is being spent on researching it. Nevertheless, the molecular self-assembly method prepares organic-inorganic hybrid thin films by using static electricity and does not represent technology that controls a monomolecular layer in a strict sense. Its low thermal stability makes it difficult to prepare a stable organic-inorganic hybrid thin film of high quality. In addition, the thermal deposition (evaporation) method prepares an organic-inorganic hybrid thin film in a gas phase and makes it difficult to control a monomolecular layer. In addition, its raw material molecules are very restricted so that its applications are also limited.

In order to solve such problems with the existing methods for preparing an organic-inorganic hybrid thin film, molecular layer deposition technology has been developed that enables not only organic polymers but also organic-inorganic hybrid materials to be deposited. The molecular layer deposition technology represents gas phase deposition in which inorganic or organic molecules can be controlled in a molecular unit based on the self-controlled surface reaction of inorganic or organic molecules. The S. M. George group as a representative example used molecular layer deposition technology to prepare the alucone polymer film with trimethyl aluminium (TMA) and ethylene glycol (EG). However, in such existing molecular layer deposition, the functional group including an organic precursor has been restricted to a hydroxyl group, a carboxyl group and their derivatives and the organic-inorganic hybrid thin film prepared accordingly has a problem such that it becomes unstable and decomposed upon standing in the air.

Currently, the encapsulation film has various forms including the single film based on inorganic materials such as $SiO_2$, SiN and $Al_2O_3$, the multi-layered film prepared by alternately depositing inorganic materials, and the multi-layered film prepared by alternately depositing inorganic materials and organic materials. While ion beam deposition, electron beam deposition, plasma beam deposition and chemical vapour deposition have been used to form inorganic passivation films, such existing techniques have problems in that their deposition temperatures must be high and that coverage of a thin film was not excellent.

Thus the atomic layer deposition (ALD) method that enables the formation of a passivation film at low temperatures has been receiving much attention. ALD represents the ideal technology for preparing inorganic and metallic thin films in which a self-controlled reaction is used in an atomic unit to deposit a mono atomic layer and may be considered to be a deposition technique of a new concept that enables control of the thickness of a mono atomic layer. However, it has not achieved the desired performance yet because of the pin hole taking place during the process of passivation film formation.

In addition, Vitex Systems of USA manufactured a flexible substrate with superior gas barrier properties wherein a process, in which a monomeric thin film is formed on a polymeric substrate film, and UV is irradiated therein to carry out a polymerization reaction to achieve high molecular weights (solidified organic layer) to form a coating layer by the methods of PECVD, CVD, etc., and an inorganic thin film is formed over it by sputtering, is repeated to prepare a number of organic-inorganic layers.

However, while a plastic substrate has been presented whose gas and moisture blocking characteristics have been improved by the above gas barrier film, it has the problem that its gas and moisture blocking characteristics and surface hardness are too low to be used for applications including OLED and LCD.

DETAILED DESCRIPTION OF THE INVENTION

Technical Task

The present invention has as its objective to solve the problems with the prior art above and to provide a substrate structure including a new stable organic-inorganic hybrid thin film in which a precursor compound used for forming an inorganic layer and a precursor compound used for forming an organic layer including a new functional group are alternately used.

The present invention also has as its objective to provide a method for preparing the substrate structure according to the present invention.

Means for Task Solution

The present invention provides the substrate structure comprising a substrate and an organic-inorganic hybrid thin film expressed by the formula 1 that is laminated over the substrate below to solve the tasks above.

$$-[M-X-R1-Y-]_m-$$ [Formula 1]

(In the formula 1 above m is 1 or more,

R1 is $C_{1\sim20}$ alkyl, $C_{5\sim20}$ cycloalkyl, or aryl or heteroaryl of 5~60 nuclear atoms, M is selected from a group consisting of Zn, Sn, In, Cd, Ga, Al, Ti, Si, V, Mn, Fe, Co, Cu, Zr, Ru, Mo, Nb and W, and X or Y is selected from a group consisting of O, S, N, NH and CO, and either X or Y is S.)

In the substrate structure according to the present invention, the thickness of the organic-inorganic hybrid thin film characteristically ranges from 1 A to 500 A.

In the substrate structure according to the present invention, assuming that the initial thickness of the organic-inorganic hybrid thin film is d0 and that the thickness of the organic-inorganic hybrid thin film after standing under the STP conditions for n hours is dn, the relation equation below is satisfied:

$$0 \le (dn/d0) \le 0.1 (0 \le n \le 240)$$

The structure of the substrate structure according to one example of the present invention is shown in FIG. 1. As is shown in FIG. 1, the substrate structure according to one example of the present invention comprises a substrate (10); and an organic-inorganic hybrid thin film (20) that is formed on top of the substrate.

In the substrate structure according to the present invention, the substrate (10) is a conductive transparent substrate selected from a group consisting of ITO, FTO, ZnO, CdO, CdSe and CdS.

In the substrate structure according to the present invention, the substrate is a polymeric substrate selected from a group consisting of fluoropolymer resin, polyester, polyacrylate, polyamide, polyimide and polycarbonate.

In the substrate structure according to the present invention, the polymeric substrate is selected from a group consisting of polyvinylidene fluoride (PVDF), polyethylene terephthalate (PET), polyethylene naphthalate (PEN) and polymethyl methacrylate (PMMA).

In the substrate structure according to the present invention, the thickness of the organic-inorganic hybrid thin film (20) ranges from 1 A to 500 A.

In the substrate structure according to the present invention, assuming that the initial thickness of the organic-inorganic hybrid thin film is d0 and that the thickness of the organic-inorganic hybrid thin film after standing under the STP conditions for n hours is dn, the relation equation below is satisfied:

$$0 \le (dn/d0) \le 0.1 (0 \le n \le 240)$$

The present invention also provides a substrate structure comprising a substrate, a substrate structure including an organic-inorganic hybrid thin film laminated on the substrate and a functional thin film including an oxide layer of a metal selected from a group consisting of Zn, Sn, In, Cd, Ga, Al, Ti, Si, V, Mn, Fe, Co, Cu, Zr, Ru, Mo, Nb and W.

In FIG. 2 is shown a substrate structure including the functional thin film according to another example of the present invention. As is shown in FIG. 2, the functional thin film comprises an organic-inorganic hybrid thin film (20) and an oxide layer (30). That is, the substrate structure comprises a substrate (10) and an organic-inorganic hybrid thin film (20) laminated on the substrate; and an oxide layer (30) of a metal selected from a group consisting of Zn, Sn, In, Cd, Ga, Al, Ti, Si, V, Mn, Fe, Co, Cu, Zr, Ru, Mo, Nb and W that is laminated on top of the organic-inorganic hybrid thin film.

In the substrate structure including the functional thin film according to the present invention, the thickness of the metal oxide layer (30) of a metal selected from a group consisting of Zn, Sn, In, Cd, Ga, Al, Ti, Si, V, Mn, Fe, Co, Cu, Zr, Ru, Mo, Nb and W ranges from 10 A to 2000 A.

In the substrate structure including the functional thin film according to the present invention, assuming that the initial thickness of the substrate structure including the functional thin film is D0 and that the thickness of the substrate structure after standing under the STP (standard temperature and pressure) conditions for n hours is Dn, the relation equation below is satisfied:

$$0 \le (Dn/D0) \le 0.1 (0 \le n \le 240)$$

In FIG. 3 to FIG. 6 are illustrated the substrate structures according to other examples of the present invention.

As is shown in FIG. 3, the substrate structure according to the present invention can further include a first chemical resistant layer (40) between the substrate (10) and the organic-inorganic hybrid thin film (20).

As is shown in FIG. 4, the substrate structure according to the present invention can further include a second chemical resistant layer (50) below the substrate (10).

In the substrate structure according to the present invention, the first chemical resistant layer (40) and second chemical resistant layer (50) can include at least one species of resin selected from acrylic resin, epoxy resin, polysilazane and polyimide resin.

As are shown in FIG. 5 and FIG. 6, the substrate structure according to the present invention can further include a protective layer (60) on top of the organic-inorganic hybrid thin film (20) and/or on top of the metal oxide layer (30). The protective layer can include polyimide.

The present invention also provides the electronic device including the substrate structure according to the present invention, for example, a light emitter, display or solar battery cell.

The present invention also provides a method for preparing a substrate structure comprising, (1) a step in which the first precursor compound expressed by the formula 2 below is used to form an inorganic molecular layer; and $$M(R21)(R22)\ldots(R2n) \qquad \text{[Formula 2]}$$

(In the Formula 2 above M is selected from a group consisting of Zn, Sn, Cd, Ti, Si, V, Mn, Fe, Co, Cu, Zr, Ru, Mo, Nb, W, In, Ga, Al and Tl, n is determined according to the oxidation number state of the metal M, and R21 to R2n are each independently $C_{1\sim20}$ alkyl, $C_{1\sim20}$ alkoxide, a chloride group, a hydroxide group, an oxyhydroxide group, a nitrate group, a carbonate group, an acetate group or an oxalate group.)

(2) a step in which the second precursor compound expressed by the formula 3 below is reacted with the inorganic molecular layer to form an organic molecular layer over the inorganic molecular layer.

$$R3\text{-}S\text{—}R4\text{-}R5 \qquad \text{[Formula 3]}$$

(In the Formula 3 above, R3 is hydrogen, COR6, $C_{1\sim20}$ alkyl, $C_{5\sim20}$ cycloalkyl, or aryl or heteroaryl of 5~60 nuclear atoms, R4 is $C_{1\sim20}$ alkyl, $C_{5\sim20}$ cycloalkyl, or aryl or heteroaryl of 5~60 nuclear atoms, R5 is one or more species selected from a group consisting of a $C_{1\sim20}$ alkoxy group, an ether group, a carboxylic group, COR6, a thiol group and an amine group, and R6 is one or more species selected from a group consisting of hydrogen, an alkoxy group, an ether group, a carboxylic group, a thiol group, and an amine group.)

In the method for preparing the substrate structure according to the present invention, the first precursor compound is reacted with a substrate to form an inorganic layer on the substrate surface.

The first precursor compound can be any precursor that enables an inorganic thin film to be formed, and a metallic compound having high vapour pressure is used to inject a desired amount of the precursor into a chamber in a short period. For example, the first precursor compound can be a group consisting of alkoxide, chloride, hydroxide, oxyhydroxide, nitrate, carbonate, acetate, oxalate and their mixtures that includes one species of a metal selected from a group consisting of Zn, Sn, In, Cd, Ga, Al, Ti, Si, V, Mn, Fe, Co, Cu, Zr, Ru, Mo, Nb and W and their combinations as the metal M.

The first precursor compound characteristically comprises n substituents of R21, R22 . . . R2n that are determined according to the oxidation number state of the metal M wherein R21 to R2n are each independently $C_{1\sim20}$ alkyl, $C_{1\sim20}$ alkoxide, a chloride group, a hydroxide group, an oxyhydroxide group, a nitrate group, a carbonate group, an acetate group or an oxalate group.

Specifically, raw material gases used for forming the inorganic layer including a Zn metal include DEZn (diethyl zinc), and DMZn (dimethyl zinc), while the raw material gases used for forming the inorganic layer including an Al metal can be trimethyl aluminium (TMA), triethyl aluminium (TEA), etc.

In the method for preparing the substrate structure according to the present invention, SR3 or R5 of the second precursor compound expressed by the formula 3 above reacts with the inorganic layer formed on the substrate surface by the first precursor compound to form an organic-inorganic hybrid thin film.

In the method for preparing the substrate structure according to the present invention, the compound expressed by the formula 4 can be used for the second precursor compound.

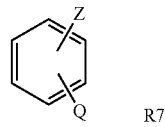

[Formula 4]

(In the formula 4, Z is a thiol group, Q is any one selected from a thiol group and a hydroxyl group, and Z and Q are located at the ortho, meta or para position.)

In the method for preparing the organic-inorganic hybrid thin film according to the present invention, the compound expressed by the formula 5 or formula 6 below can be used for the second precursor compound.

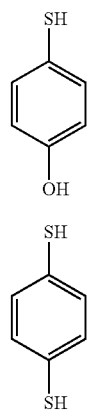

[Formula 5]

[Formula 6]

In the method for preparing the substrate structure according to the present invention, the step (1) and step (2) can be repeatedly performed to form the organic-inorganic hybrid thin film at a desired thickness.

The method for preparing the substrate structure according to the present invention further includes a step in which an oxide layer is formed over the substrate surface prior to step (1).

The present invention also provides a method for preparing a substrate structure comprising a functional thin film that further includes a step (3) in which an oxide layer of a metal selected from a group consisting of Zn, Sn, In, Cd, Ga, Al, Ti, Si, V, Mn, Fe, Co, Cu, Zr, Ru, Mo, Nb and W is formed by atomic layer deposition after an organic-inorganic hybrid thin film is formed by step (1) and step (2).

In the method for preparing the substrate structure comprising a functional thin film according to the present invention, step (3) is repeatedly performed n2 times (n2 is 1 or more) after each of steps (1) and (2) has repeatedly been performed n1 times (n1 is 1 or more).

In the method for preparing the substrate structure comprising a functional thin film according to the present invention, the steps (1) to (3) are repeatedly performed.

Effects of the Invention

Because the substrate structure comprising the organic-inorganic hybrid thin film according to the present invention includes not only the organic-inorganic hybrid thin film but also a new functional group so as to remain stable in air, it can be applied to various fields including nano patterning for manufacturing semiconductors and electronic devices, chemical sensors and biosensors, nano tribology, surface modification, nano electronic machine systems (NEMS), micro electronic machine systems (MEMS) and non-volatile memory.

The method for preparing the substrate structure comprising the organic-inorganic hybrid thin film according to the present invention enables provision of a very stable organic-inorganic hybrid multi-layered molecular film in air by including a new functional group not used previously in its organic precursor when preparing the organic-inorganic hybrid thin film by alternately using organic precursor and inorganic precursor according to the molecular layer deposition method.

BRIEF DESCRIPTION OF THE DRAWINGS

FIG. 1 to FIG. 6 schematically show the substrate structures according to examples of the present invention.

FIG. 7 and FIG. 8 respectively show thin film growth rates versus the injection amounts of first precursor and second precursor in one example of the present invention.

FIG. 9 shows results of the ultraviolet spectroscopic measurement on the organic-inorganic hybrid thin film and 4-mercapto phenol prepared in one example of the present invention.

FIG. 10 shows results of the UV-Vis absorption measurement on the organic-inorganic hybrid thin film prepared in one example of the present invention.

FIG. 11 shows results of the air stability test on the organic-inorganic hybrid thin film prepared in one example of the present invention and the thin film prepared in the comparative example.

FIG. 12 shows results of the thin film thickness measurement versus the cycle of the organic-inorganic hybrid thin film formation process in one example of the present invention.

FIG. 13 shows results of the surface roughness measurement on the hybrid thin film prepared in one example of the present invention.

FIG. 14 and FIG. 15 respectively show thin film growth rates versus the injection amounts of first precursor and second precursor in one example of the present invention.

FIG. 16 shows results of the ultraviolet spectroscopic measurement on the organic-inorganic hybrid thin film prepared in one example of the present invention.

FIG. 17 shows results of the UV-Vis absorption measurement on the organic-inorganic hybrid thin film prepared in one example of the present invention.

FIG. 18 shows results of the air stability test on the organic-inorganic hybrid thin film prepared in one example of the present invention and the thin film prepared in the comparative example.

FIG. 19 shows results of the thin film thickness measurement of the organic-inorganic hybrid thin film formation process in one example of the present invention.

FIG. 20 shows results of the surface roughness measurement on the hybrid thin film prepared in one example of the present invention.

FIG. 21 shows results of the TEM photograph measurement on the organic-inorganic hybrid super-lattice thin film prepared in one example of the present invention.

FIG. 22 and FIG. 23 show the rate of pinhole formation inhibition measured by varying the thickness of an organic-inorganic hybrid thin film in the organic-inorganic hybrid super-lattice thin film prepared in one example of the present invention.

FIG. 24 shows results of the thin film stress measurement versus the ratio of the $Al_2O_3$ thin film formed by atomic layer deposition to the organic-inorganic hybrid thin film in the organic-inorganic hybrid super-lattice thin film prepared in one example of the present invention.

FIG. 25 shows results of the Ca test on the organic-inorganic hybrid thin film prepared in one example of the present invention and the thin film prepared in the comparative example.

SPECIFIC DETAILS FOR IMPLEMENTING THE INVENTION

The present invention is described in further detail below according to examples of the present invention. However, the present invention is not limited to the examples below.

Example 1

After an Si (100) substrate was washed with distilled water and acetone, it was purged with $N_2$ gas 2-3 times to remove any contaminants on the substrate surface before diethyl zinc (DEZn) was used as a first precursor compound to deposit a diethyl zinc (DEZn) thin film over the Si substrate according to the molecular layer deposition method.

Over the diethyl zinc (DEZn) thin film was formed an organic molecular film by using 4-mercapto phenol as a second precursor compound according to the molecular layer deposition method to prepare an organic-inorganic hybrid thin film. Argon was used for both carrier gas and purging gas, and DEZn and 4-mercapto phenol were respectively evaporated at 20° C. and 70° C. One cycle was achieved by exposure to DEZn for 2 seconds, purging with Ar for 10 seconds, exposure to 4-mercapto phenol for 2 seconds and purging with Ar for 50 seconds. The thin film was grown at a temperature of 80° C. to 200° C. and under a pressure of 300 mTorr.

<Experiment> Measurement of Growth Rates Versus Injection Time of Organic Precursor and Inorganic Precursor In Example 1, growth rates of the thin film according to the injection time of the first precursor compound of diethyl zinc (DEZn) and growth rates of the thin film according to the injection time of the second precursor compound of 4-mercapto phenol were measured and respectively shown in FIG. 7 and FIG. 8.

It may be noted from FIG. 7 and FIG. 8 that growth rates of the thin films increased with injection amounts of the first precursor compound of diethyl zinc (DEZn) and the second precursor compound of 4-mercapto phenol and then the growth rates no longer increased but remained at certain rates.

<Experiment> IR Spectroscopic Measurement

IR spectroscopic measurements were made on the organic-inorganic hybrid thin film prepared by the same method as Example 1 except that KBr pellets were used instead of the Si substrate and 4-mercapto phenol, and the results are shown in FIG. 9.

It may be verified in FIG. 9 that a hydroxyl group and a thiol group of 4-mercapto phenol are found in the comparative example in which only 4-mercapto phenol is included whereas in the case of the organic-inorganic hybrid thin film according to the present invention, the hydroxyl group and the thiol group of mercapto phenol used as its second precursor react with the inorganic molecular layer prepared by its first precursor to form a hybrid thin film so that the hydroxyl group and thiol group of mercapto phenol are not detected by the infrared spectroscopic method.

<Experiment> UV-VIS Spectroscopic Measurement

UV-Vis absorption on the organic-inorganic hybrid thin film prepared in Example 1 above was measured and the results are shown in FIG. 10. It may be verified from FIG. 10 that the organic-inorganic hybrid thin film according to the present invention has no absorption in the visible ray range.

Comparative Example

In a comparative example an organic-inorganic hybrid thin film was prepared the same way as in Example 1 above except that diethyl zinc (DEZn) was used as its first precursor compound to deposit a diethyl zinc (DEZn) thin film oven an Si substrate according to the molecular layer deposition method and then hydroquinone (HQ) was used as its second precursor compound.

<Experiment> Stability Test in Air

While the organic-inorganic hybrid thin film of Example 1 and the organic-inorganic hybrid thin film prepared in the Comparative Example above were left in air, changes in their thicknesses were measured to test stability in air, and the results are shown in FIG. 11.

It may be realized in FIG. 11 that unlike in the present invention the thickness drastically decreases in the case of the Comparative Example that does not include an S group whereas the thickness does not change with time in the case of the Example according to the present invention and that the organic-inorganic hybrid multi-layered film including an S group is very stable in air.

Example 2

As in Example 1 above, diethyl zinc (DEZn) was used as the first precursor compound to deposit a thin film over an Si substrate and 4-mercapto phenol was used as the second precursor compound to form an organic-inorganic hybrid thin film over the diethyl zinc (DEZn) thin film according to the molecular layer deposition method before the process of forming the diethyl zinc (DEZn) by the first precursor compound, and while the thin film based on the second precursor compound was repeatedly formed, thicknesses of the thin film were measured and the results are shown in FIG. 12.

It may be verified in FIG. 12 that the number of repetitions for the process of forming the thin film by the first precursor compound and forming the thin film by the second precursor compound is proportional to the thickness of the thin film formed.

<Experiment> Surface Roughness Measurement

The organic-inorganic hybrid thin film of 50 nm in the thickness prepared in Example 2 was measured for its surface roughness with AFM, and the results are shown in FIG. 13. The average roughness measured was 2.2 A.

Example 3

After an Si (100) substrate was washed with distilled water and acetone, it was purged with $N_2$ gas 2-3 times to remove any contaminants on the substrate surface before trimethyl aluminium (TMA) was used as a first precursor compound to deposit a trimethyl aluminium (TMA) thin film over the Si substrate according to the molecular layer deposition method.

Over the trimethyl aluminium (TMA) thin film was formed an organic molecular film by using 4-mercapto phenol as a second precursor compound according to the molecular layer deposition method to prepare an organic-inorganic hybrid thin film.

Argon was used for both carrier gas and purging gas, and TMA and 4-mercapto phenol were respectively evaporated at 20° C. and 70° C. One cycle was achieved by exposure to TMA for 2 seconds, purging with Ar for 10 seconds, exposure to 4-mercapto phenol for 2 seconds and purging with Ar for 50 seconds. The thin film was grown at a temperature of 80° C. to 200° C. and under a pressure of 300 mTorr.

<Experiment> Measurement of Growth Rates Versus Injection Time of Organic Precursor and Inorganic Precursor In Example 3, growth rates of the thin film according to the injection time of the first precursor compound of trimethyl aluminium (TMA) and growth rates of the thin film according to the injection time of the second precursor compound of 4-mercapto phenol were measured and respectively shown in FIG. 14 and FIG. 15.

It may be noted from FIG. 14 and FIG. 15 that growth rates of the thin films increased with injection amounts of the first precursor compound of trimethyl aluminium (TMA) and the second precursor compound of 4-mercapto phenol and then the growth rates no longer increased but remained at certain rates.

<Experiment> IR Spectroscopic Measurement

IR spectroscopic measurements were made on the organic-inorganic hybrid thin film prepared by the same method of Example 3 except that KBr pellets were used instead of the Si substrate and 4-mercapto phenol, and the results are shown in FIG. 16.

It may be verified in FIG. 16 that in the case of the organic-inorganic hybrid thin film according to the present invention, the hydroxyl group and the thiol group of mercapto phenol used as its second precursor react with the inorganic molecular layer prepared by its first precursor to form a hybrid thin film so that the hydroxyl group and the thiol group of mercapto phenol are not detected by the infrared spectroscopic method.

<Experiment> UV-VIS Spectroscopic Measurement

UV-Vis absorption on the organic-inorganic hybrid thin film prepared in Example 3 above was measured and the results are shown in FIG. 17. It may be verified from FIG. 17 that the organic-inorganic hybrid thin film according to the present invention has no absorption in the visible ray range.

Comparative Example

In a comparative example an organic-inorganic hybrid thin film was prepared in the same way as in Example 3 above except that trimethyl aluminium (TMA) was used as its first precursor compound to deposit a trimethyl aluminium (TMA) thin film oven an Si substrate according to the molecular layer deposition method and then hydroquinone (HQ) was used as its second precursor compound.

<Experiment> Stability Test in Air

While the organic-inorganic hybrid thin film of Example and the organic-inorganic hybrid thin film prepared in the Comparative Example above were left in air, changes in their thicknesses were measured to test stability in air, and the results are shown in FIG. 18.

It may be recognized in FIG. 12 that, assuming that the initial thickness is d0 and the thickness in n hours is dn, dn/d0 in the case of the Comparative Example without including the S group increases to 0.5 or more as a result of a drastic decrease in its thickness unlike in the present invention whereas in the case of the Example according to the present invention, dn/d0 is kept at 0.1 or less as a result of the absence of changes in its thickness with time and that the organic-inorganic hybrid thin film according to the present invention is very stable in air.

Example 4

As in Example 3 above, trimethyl aluminium (TMA) was used as the first precursor compound to deposit a thin film over an Si substrate and 4-mercapto phenol was used as the second precursor compound to form an organic-inorganic hybrid thin film over the trimethyl aluminium (TMA) thin film according to the molecular layer deposition method before the process of forming the trimethyl aluminium (TMA) thin film by the first precursor compound, and while the thin film based on the second precursor compound was repeatedly formed, thicknesses of the thin film were measured and the results are shown in FIG. 19.

It may be verified in FIG. 19 that the number of repetitions for the process of forming the thin film by the first precursor compound and forming the thin film by the second precursor compound is proportional to the thickness of the thin film formed.

<Experiment> Surface Roughness Measurement

The organic-inorganic hybrid thin film of 50 nm in the thickness prepared in Example 4 was measured for its surface roughness with AFM, and the results are shown in FIG. 20. The average roughness measured was 2.8 A.

Example 5

After an organic-inorganic hybrid thin film was prepared in the same way as in Examples 1 and 3 above, an $Al_2O_3$ thin film was deposited over the organic-inorganic hybrid thin film according to the atomic layer deposition method, and such a process was repeated by controlling the ratio of the $Al_2O_3$ thin film based on atomic layer deposition to the organic-inorganic hybrid thin film according to the present invention to prepare an organic-inorganic hybrid functional thin film.

In order to form the $Al_2O_3$ thin film according to atomic layer deposition, argon gas was used as carrier gas and purging gas, and trimethyl aluminium (TMA) and $H_2O$ were evaporated at normal temperature. Its cycle was achieved by exposure to TMA for 1 second, purging with Ar for 5 seconds, exposure to $H_2O$ for 1 second and purging with Ar for 5 seconds. The above thin film was grown at a temperature of 80° C. under a pressure of 300 mTorr.

<Experiment> TEM Measurement

The TEM photograph was measured when the ratio of the organic-inorganic hybrid thin film:$Al_2O_3$ thin film prepared in Example 5 above was 1:2, and the results are shown in FIG. 21. It may be verified in FIG. 21 that the $Al_2O_3$ thin film according to atomic layer deposition and the organic-inorganic hybrid thin film according to the present invention were alternately formed.

<Experiment> Measurement of Pinhole Formation Inhibition Effects

In Example 5 above, rates of pinhole formation inhibition were measured by varying the thickness of the organic-inorganic hybrid thin film, and the results are shown in FIG. 22 and FIG. 23.

It may be realized in FIG. 23 that pinholes are seldom formed if the thickness of the organic-inorganic hybrid thin film according to the present invention is 80 nm or more.

<Experiment> Thin Film Stress Measurement

In the organic-inorganic hybrid functional thin film prepared in Example 5 above, thin film stress was measured versus the ratio of the $Al_2O_3$ thin film to the organic-inorganic hybrid thin film according to the present invention while the total thickness of the thin film was kept the same, and the results are shown in FIG. 24.

<Experiment> Measurements of Moisture Permeability Resistance and Oxygen Permeability Resistance The organic-inorganic hybrid functional thin film prepared in Example 5 above, and the $Al_2O_3$ thin film of the Comparative Example were measured for their moisture permeability resistance and oxygen permeability resistance, and the results are listed in Table 1 and FIG. 25 below.

It may be noted from Table 1 and FIG. 25 below that the functional thin film comprising the organic-inorganic hybrid thin film and $Al_2O_3$ according to the present invention has superior moisture permeation resistance and oxygen permeation resistance to those of the Comparative Example.

TABLE 1

| Barrier Film (nm) | WVTR (g/m² day) | OTR (cm³/m² day) |
|---|---|---|
| $Al_2O_3$ (100 nm) | $3.11 \times 10^{-7}$ | $9.66 \times 10^{-5}$ |
| Organic/$Al_2O_3$ super lattice (100 nm) | $2.68 \times 10^{-7}$ | $8.33 \times 10^{-5}$ |

INDUSTRIAL VIABILITY

Because the substrate structure comprising the organic-inorganic hybrid thin film according to the present invention includes a new functional group so as to remain stable in air, it can be not only used for encapsulation of light emitters, displays and solar battery cells but also applied to various fields including nano patterning for manufacturing semiconductors and electronic devices, chemical sensors and biosensors, nano tribology, surface modification, nano electronic machine systems (NEMS), micro electronic machine systems (MEMS) and non-volatile memory.

The method for preparing the organic-inorganic hybrid thin film according to the present invention enables provision of a very stable organic-inorganic hybrid multi-layered molecular film in air by including a new functional group not used previously in its organic precursor when preparing the organic-inorganic hybrid thin film by alternately using organic precursor and inorganic precursor according to the molecular layer deposition method.

The invention claimed is:
1. A substrate structure comprising:
   a substrate; and
   hybrid organic/inorganic thin films stacked on the substrate, the hybrid organic/inorganic thin films being represented by the following Formula 1:

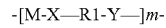 [Formula 1]

wherein in Formula 1,
   m is 1 or more,
   R1 is a substituted or unsubstituted aryl or heteroaryl having a nuclear atomic number of 5-60, M is selected from the group consisting of Zn, Sn, In, Cd, Ga, Al, Ti, Si, V, Mn, Fe, Co, Cu, Zr, Ru, Mo, Nb, and W, one of X and Y is O, and the other is S.

2. The substrate structure of claim 1, wherein a thickness of the hybrid organic/inorganic thin films is from 1 Å to 500 Å.

3. The substrate structure of claim 1, wherein the following relationship is satisfied when an initial thickness of the hybrid organic/inorganic thin films is set to do, and a thickness of the hybrid organic/inorganic thin films after standing under STP conditions for n hours is set to dn:

$$0 \le (dn/d0) \le 0.1 (0 \le n \le 240),$$

wherein d0 and dn are measured under STP conditions.

4. The substrate structure comprising functional thin films comprising the hybrid organic/inorganic thin films as claimed in claim 1 and further comprising an oxide layer of a metal selected from the group consisting of Zn, Sn, In, Cd, Ga, Al, Ti, Si, V, Mn, Fe, Co, Cu, Zr, Ru, Mo, Nb, and W, formed on or under the hybrid organic/inorganic thin films.

5. The substrate structure of claim 4, wherein a thickness of the oxide layer of a metal is from 100 Å to 2,000 Å.

6. The substrate structure of claim 4, wherein the following relationship is satisfied when an initial thickness of the substrate structure is set to D0, and a thickness of the substrate structure after standing under STP conditions for n hours is set to Dn:

$$0 \le (Dn/D0) \le 0.1 (0 \le n \le 240),$$

wherein d0 and do are measured under STP conditions.

7. The substrate structure of claim 1, wherein the substrate is a conductive and transparent substrate selected from the group consisting of ITO, FTO, ZnO, AZO, CdO, and $TiO_2$.

8. The substrate structure of claim 1, wherein the substrate is a polymer substrate selected from the group consisting of a fluoropolymer resin, polyester, polyacrylate, polyamide, polyimide, and polycarbonate.

9. A light-emitting body comprising the substrate structure as claimed in claim 1.

10. A display apparatus comprising the substrate structure as claimed in claim 1.

11. A photovoltaic device comprising the substrate structure as claimed in claim 1.

12. A method of manufacturing a substrate structure as claimed in claim 1, the method comprising:
(1) forming an inorganic molecular layer on a surface of a substrate using a first precursor compound represented by the following Formula 2:

M(R21)(R22) ... (R2n)     [Formula 2]

wherein in Formula 2,
M is selected from the group consisting of Zn, Sn, Cd, Ti, Si, V, Mn, Fe, Co, Cu, Zr, Ru, Mo, Nb, W, In, Ga, Al, and Tl,
n is determined as claimed in an oxidation number of a metal M, and
R21 to R2n are each independently $C_{1-20}$ alkyl, $C_{1-20}$ alkoxide, a chloride group, a hydroxyl group, an oxyhydroxide group, a nitrate group, a carbonate group, an acetate group, or an oxalate group; and
(2) forming an organic molecular layer on the inorganic molecular layer via a reaction of a second precursor compound represented by the following Formula 3 with the inorganic molecular layer:

R3-S—R4-R5     [Formula 3]

wherein in Formula 3,
R3 is hydrogen, COR6, $C_{1-20}$ alkyl, $C_{5-20}$ cycloalkyl, or aryl or heteroaryl of nuclear atomic number of 5-60,
R4 is $C_{1-20}$ alkyl, $C_{5-20}$ cycloalkyl, or aryl or heteroaryl of nuclear atomic number of 5-60,
R5 is at least one selected from the group consisting of a hydroxyl group, a $C_{1-20}$ alkoxy group, an ether group, a carboxyl group, COR6, a thiol group, and an amine group, and
R6 is at least one selected from the group consisting of hydrogen, an alkoxy group, an ether group, a carboxyl group, a thiol group, and an amine group.

13. The method of manufacturing a substrate structure of claim 12, wherein the second precursor compound is represented by the following Formula 4:

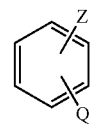

[Formula 4]

wherein in Formula 4, Z is a thiol group, Q is one selected from a thiol group or a hydroxyl group, and Z and Q are at an ortho, meta, or para position.

14. The method of manufacturing a substrate structure as claimed in claim 13, wherein the second precursor compound is represented by the following Formula 5:

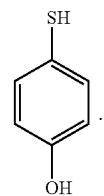

[Formula 5]

15. The method of manufacturing a substrate structure as claimed in claim 13, wherein the second precursor compound is represented by the following Formula 6:

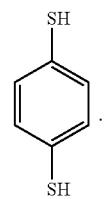

[Formula 6]

16. The method of manufacturing a substrate structure as claimed in claim 12, further comprising repeatedly conducting (1) and (2).

17. The method of manufacturing a substrate structure as claimed in claim 12, further comprising forming an oxide layer on a surface of the substrate prior to (1).

18. The method of manufacturing a substrate structure having functional thin films of claim 12, the method further comprising (3) forming an oxide layer of a metal selected from the group consisting of Zn, Sn, In, Cd, Ga, Al, Ti, Si, V, Mn, Fe, Co, Cu, Zr, Ru, Mo, Nb, and W by an atomic layer deposition method.

19. The method of manufacturing a substrate structure of claim 12, that comprises repeatedly conducting (1) and (2) n1 times where n1 is 1 or more, and then, (3) n2 times wherein n2 is 1 or more.

20. The method of manufacturing a substrate structure of claim 19, comprising repeatedly conducting (1) to (3).

* * * * *